United States Patent [19]

Vince

[11] Patent Number: 5,056,519
[45] Date of Patent: Oct. 15, 1991

[54] UNILATERAL DIAPHRAGMATIC PACER

[76] Inventor: Dennis J. Vince, 610-943 West Broadway, Vancouver, British Columbia V5Z 1K3, Canada

[21] Appl. No.: 522,778

[22] Filed: May 14, 1990

[51] Int. Cl.$^5$ ............................................. A61N 1/36
[52] U.S. Cl. ............................................. 128/419 G
[58] Field of Search .................... 128/419 G, 421, 723

[56] References Cited

U.S. PATENT DOCUMENTS 4,827,935  5/1989  Geddes et al. ................ 128/419 G

OTHER PUBLICATIONS

"A Heart-Rate-Responsive Diaphragm Pacemaker", Med. & Biol. Eng. & Computing, Kimura et al., 1987, 25, 458–462.

*Primary Examiner*—William E. Kamm
*Assistant Examiner*—Scott M. Getzon

[57] ABSTRACT

An apparatus to innervate a deinnervated lung diaphragm and pace the deinnervated diaphragm with a normal innervated lung diaphragm. The apparatus has a sensing device sense operation of normal innervated lung diaphragm. The device produces a signal representative of the operation of the normal innervated diaphragm. The signal is modified in accordance with a set pattern to provide a modified signal showing the rate and duration of inspiration for the normal, innervated diaphragm. A pulse generator is fed by the modified signal to produce a pulse. A stimulator innervates the deinnervated diaphragm at the same rate and duration as a normal innervated lung diaphragm. A method of operating the apparatus is also described.

12 Claims, 1 Drawing Sheet

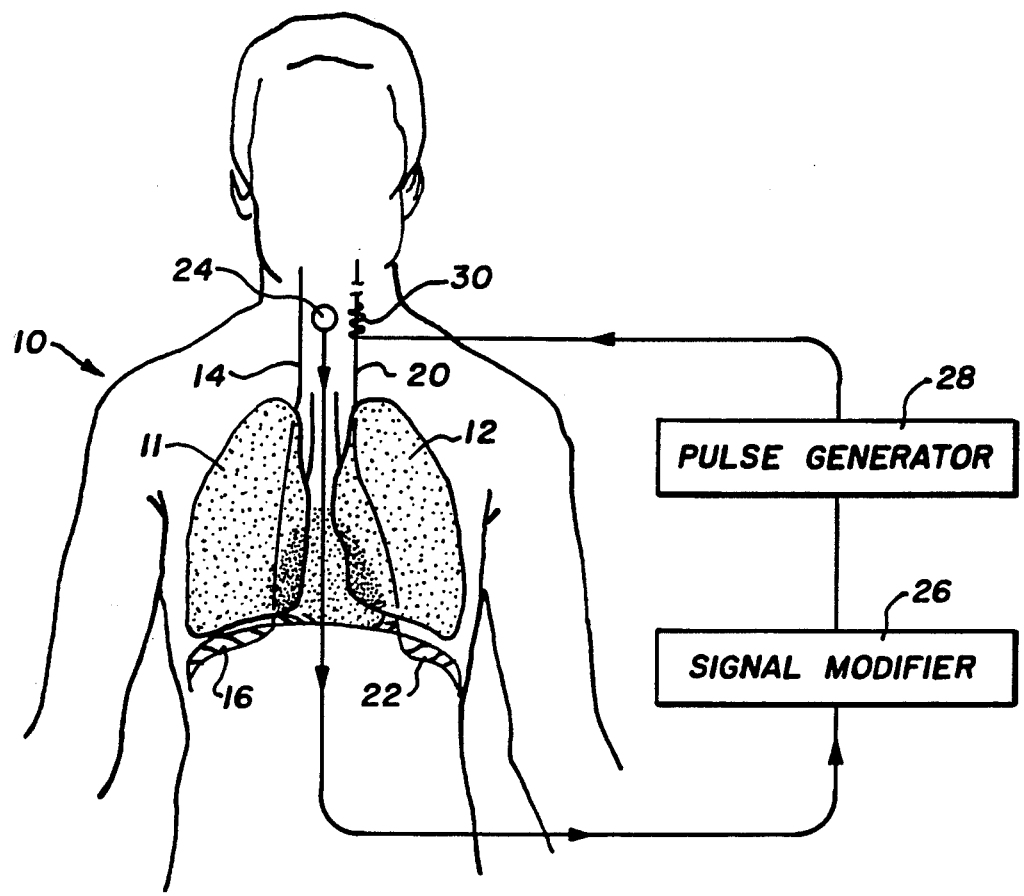

UNILATERAL DIAPHRAGMATIC PACER

FIELD OF THE INVENTION

The present invention relates to an apparatus to innervate a deinnervated lung diaphragm and unilaterally pace the deinnervated diaphragm to the normal innervated diaphragm.

DESCRIPTION OF THE PRIOR ART

For a person who has lost innervation of one of the lung diaphragms as a result of trauma, surgical damage, acquired disease of congenital malformation, the prior art permits the electrical pacing of the deinnervated diaphragm by producing an electrical stimulus which intermittently stimulates the diaphragm to contract by electrically stimulating the phrenic nerves innervating that diaphragm or by stimulating the diaphragm muscle directly. However the prior art does not synchronize the contraction of the deinnervated diaphragm with the normally innervated diaphragm. This generally results in asynchrony which provides inefficient respiratory efforts, since normal respiratory physiology requires synchronous contraction of both diaphragms.

Patients who have a deinnervated diaphragm are living by virtue of their innervated diaphragm. For this reason, it is undesirable to interfere in any way with the innervated diaphragm or the innervated nerve supply to the innervated diaphragm muscle, since any disruption may result in bilateral diaphragmatic paralysis and the patient would then be dependent upon a respirator.

Attempts have been made to use the phrenic nerve of the innervated diaphragm as an indicator of diaphragmatic contraction and inspiration, and transmit a signal representing contraction rate and duration to a pulse generator for providing a pulse to the deinnervated diaphragm. These attempts have not been clinically acceptable because of the possibility of bilateral diaphragmatic paralysis that could occur if the normal phrenic nerve was damaged by the sensing device.

SUMMARY OF THE INVENTION

The present invention provides a sensor within the body of a patient that indicates the contraction of the innervated diaphragm. The sensor senses the functioning of the innervated diaphragm as it contracts to produce inspiration. A signal from the sensor is transmitted to a signal modifier which generates an appropriate command to a diaphragmatic pulse generator. This pulse signals either the deinnervated distal phrenic nerve or the deinnervated diaphragmatic muscle and results in contraction of the deinnervated diaphragm. The signal modifier commands the rate and duration of the pulse and is modified in accordance with a predetermined pattern or an algorithm. As this is controlled by the contraction of the innervated diaphragm, the deinnervated diaphragm tracks the normally innervated diaphragm which in turn responds to the different physiological demands of the diaphragms as indicated by the central nervous system of the body. This variation in the rate and duration of respiration for the innervated diaphragm is tracked and substantially synchronous contraction of both diaphragms occurs.

The sensor may be a temperature sensing device adapted to be located in an upper air way passage to the normal innervated lung diaphragm to produce a signal representative of temperature change resulting from an inspiration of colder air. In further embodiments the sensor may be a device able to sense skeletal muscle pressure. The muscles preferably sensed are of the pharynx or the diaphragm.

Whereas the present invention provides a sensing device to sense the operation of the innervated lung diaphragm, my co-pending application Ser. No. 522,708 filed concurrently with the present application, discloses a muscle sensing device to produce a signal from the skeletal muscle representative of muscle contraction at the onset of inspiration. Furthermore, my co-pending application Ser. No. 522,779 filed concurrently with the present application discloses a system of innervating lung diaphragms from a signal modified from an electrocardiogram pick up so that the respiratory rate and duration is generated by an algorithm related to the heart rate.

The present invention provides an apparatus to innervate a deinnervated lung diaphragm and pace the deinnervated diaphragm with a normal innervated lung diaphragm, comprising:

a sensing device adapted to be located to produce a signal representative of a change resulting from normal operation of the innervated diaphragm;

means to modify the signal in accordance with a predetermined pattern to provide a modified signal representative of the rate and duration of inspiration for the normal innervated lung diaphragm;

pulse generator means fed by the modified signal to produce a pulse; and stimulating means adapted to innervate the deinnervated diaphragm at the same rate and duration as the normal innervated lung diaphragm.

The present invention also provides a method of operating an apparatus to innervate a deinnervated lung diaphragm and pace the deinnervated diaphragm with a normal innervated lung diaphragm, comprising the steps of sensing a function of the normal innervated lung diaphragm and producing a signal representative of that function;

modifying the signal in accordance with a predetermined pattern to provide a modified signal representative of the rate and duration of inspiration for the normal innervated lung diaphragm;

utilizing the modified signal with a pulse generator means to provide a pulse; and feeding the pulse to stimulating means to innervate synchronously the deinnervated diaphragm at the same rate and duration as the normal innervated lung diaphragm.

DESCRIPTION OF THE DRAWING

The FIGURE is a schematic view of one embodiment of the apparatus according to the present invention.

DESCRIPTION OF THE PREFERRED EMBODIMENT

A body 10 is shown in the FIGURE with a normal innervated right lung diaphragm 11 and a deinnervated left lung diaphragm 12. The left diaphragm 12 is illustrated as being partially collapsed. The right diaphragm distal phrenic nerve 14 stimulates the diaphragmatic muscle 16 to contract the right diaphragm 11. Similarly the left diaphragm distal phrenic nerve 20 stimulates the diaphragmatic muscle 22 to innervate the left diaphragm 12.

In order to avoid in any way interfering with the right phrenic nerve 14 for the normal innervated right diaphragm 11, a temperature sensing device 24 is located in the upper airway to the right diaphragm 11. The temperature sensor 24 may be placed within the wall of the pharynx or within the thorax. The temperature sensor 24 senses the temperature change within the body tissues resulting from the inspiration of outside air through the upper airway. This signal is modified in accordance with an algorithm in the modifying circuit 26 to a predetermined pattern representing rate and duration of respiration for the normal right diaphragm 11. The temperature sensor 24 is able to identify changes in the rate of respiration and the duration of respiration, during the inspiration of colder, outside air. The modifying circuit produces a modified signal representative of the rate and duration of inspiration, which is fed to an electrical stimulus generator 28. The generator produces a pulse which in turn is fed to subcutaneous induction coils 30 about the left distal phrenic nerve 20 for the deinnervated left diaphragm 12.

The pulse produced by the electrical stimulus generator 28 is sufficient to stimulate the left distal phrenic nerve 20 to produce contraction of the diaphragmatic muscle 22 to innervate the deinnervated left diaphragm 12. Whereas the subcutaneous induction coils 30 are shown about the left distal phrenic nerve 20 it will be apparent to those skilled in the art that electrodes may be placed directly associated with the diaphragmatic muscle 22 for the deinnervated left diaphragm 12 to produce contraction. The subcutaneous induction coils 30 are placed within the body 10 and the electrical stimulus generator 28 placed outside the body so the pulse generated is transmitted from an external induction coil to the subcutaneous induction coils 30 within the body 10.

As an alternative the pulse generator and modifier can be implanted in the patient.

In operation, the temperature sensor 24 senses the relatively cold air in the upper airway entering the normal innervated right diaphragm 11 as inspiration commences. A signal from the sensor 24 sensing duration and rate of duration, is modified utilizing the servo loop modifying circuit 26 to provide a modified signal to the electrical stimulus generator 28 which in turn provides a pulse to the induction coils 30 to stimulate the contraction of the left diaphragmatic muscles 22 for the deinnervated left diaphragm 12. This permits synchronous contraction of the unilateral deinnervated left diaphragm 12 with that of the normally innervated right diaphragm 11. Whereas the left diaphragm 12 has been shown here as the deinnervated diaphragm, it will be apparent to those skilled in the art that the innervated and deinnervated diaphragms may be reversed.

The drawings illustrate a temperature sensor 24. However, sensor 24 may equally sense pressure generated by operation of the pharyngeal muscles or pressure generated by operation of the innervated diaphragm muscle. Indeed sensor 24 may sense pressure developed by any skeletal muscle that functions in the operation of the innervated diaphragm. In those circumstances, the signal modifier 26 will be appropriately changed from that illustrated to respond to signal generated by the pressure sensor.

Various changes may be made to the embodiment disclosed herein without departing from the scope of the present invention which is limited only by the following claims.

I claim:

1. An apparatus to innervate a deinnervated lung diaphragm and pace the deinnervated diaphragm with a normal innervated lung diaphragm, comprising:
   a sensing device adapted to be located to produce a signal representative of a change resulting from normal operation of the innervated diaphragm;
   means to modify the signal in accordance with a predetermined pattern to provide a modified signal representative of the rate and duration of inspiration for the normal innervated lung diaphragm;
   pulse generator means fed by the modified signal to produce a pulse; and
   stimulating means adapted to innervate the deinnervated diaphragm at the same rate and duration as the normal innervated lung diaphragm in response to the pulse.

2. An apparatus as claimed in claim 1 in which the sensing device is able to sense skeletal muscle pressure.

3. The apparatus to innervate a deinnervated lung diaphragm according to claim 2 in which the skeletal muscles are the muscles of the pharynx or diaphragm.

4. The apparatus to innervate a deinnervated lung diaphragm according to claim 1 wherein the pulse generator means is an electrical stimulus generator and the stimulating means comprise subcutaneous induction coils.

5. The apparatus to innervate a deinnervated lung diaphragm according to claim 1 wherein the stimulating means comprises electrodes associated with a diaphragm muscle for the deinnervated diaphragm to produce synchronous contraction of the deinnervated diaphragm.

6. The apparatus to innervate a deinnervated lung diaphragm according to claim 1 wherein the pulse generator means and stimulating means comprise an electrical stimulus generator with an external induction coil to feed a pulse to subcutaneous induction coils within the body.

7. A method of operating an apparatus to innervate a deinnervated lung diaphragm and pace the deinnervated diaphragm with a normal innervated lung diaphragm, comprising the steps of
   sensing a function of the normal innervated lung diaphragm and producing a signal representative of that function;
   modifying the signal in accordance with a predetermined pattern to provide a modified signal representative of the rate and duration of inspiration for the normal innervated lung diaphragm;
   utilizing the modified signal with a pulse generator means to provide a pulse; and
   feeding the pulse to stimulating means to innervate synchronously the deinnervated diaphragm at the same rate and duration as the normal innervated lung diaphragm.

8. A method according to claim 7 that comprises sensing the temperature in an upper air passageway of a normal innervated lung diaphragm to produce a signal representative of temperature change resulting from inspiration of colder air.

9. A method according to claim 7 that comprises sensing the pressure developed by skeletal muscles.

10. A method according to claim 9 that comprises sensing the pressure developed by the muscles of the pharynz or the diaphragm.

11. The method according to claim 7 wherein the pulse provides an electrical stimulus to the deinnervated distal phrenic nerve.

12. The method according to claim 7 wherein the pulse provides an electrical stimulus to the deinnervated diaphragmatic muscle.

* * * * *